US010245720B2

(12) United States Patent
Ptak et al.

(10) Patent No.: US 10,245,720 B2
(45) Date of Patent: Apr. 2, 2019

(54) ELASTIC VIBRATING APPLIANCE HANDLE

(71) Applicants: Chris Ptak, Plymouth, MI (US); Vic Ptak, Plymouth, MI (US)

(72) Inventors: Chris Ptak, Plymouth, MI (US); Vic Ptak, Plymouth, MI (US)

(*) Notice: Subject to any disclaimer, the term of this patent is extended or adjusted under 35 U.S.C. 154(b) by 514 days.

(21) Appl. No.: 14/852,560

(22) Filed: Sep. 12, 2015

(65) Prior Publication Data
US 2016/0075009 A1 Mar. 17, 2016

Related U.S. Application Data

(60) Provisional application No. 62/049,413, filed on Sep. 12, 2014.

(51) Int. Cl.
| | |
|---|---|
| *B25G 1/10* | (2006.01) |
| *A46B 5/00* | (2006.01) |
| *A46B 13/02* | (2006.01) |
| *A46B 17/02* | (2006.01) |
| *B26B 21/52* | (2006.01) |
| *A61C 17/34* | (2006.01) |
| *A46B 15/00* | (2006.01) |

(52) U.S. Cl.
CPC .............. *B25G 1/10* (2013.01); *A46B 5/0095* (2013.01); *A46B 13/023* (2013.01); *A46B 17/02* (2013.01); *A61C 17/3481* (2013.01); *B26B 21/52* (2013.01); *A46B 15/0087* (2013.01); *A46B 2200/1066* (2013.01)

(58) Field of Classification Search
CPC ....... B25G 1/10; A46B 5/0095; A46B 13/023; A46B 17/02
See application file for complete search history.

(56) References Cited

U.S. PATENT DOCUMENTS

| 1,792,358 | A | | 2/1931 | Byers et al. | |
|---|---|---|---|---|---|
| 1,813,630 | A | | 7/1931 | McCarty | |
| 2,022,457 | A | * | 11/1935 | Brown | A61C 17/3481 15/22.4 |
| 5,283,921 | A | * | 2/1994 | Ng | A61C 17/22 15/145 |
| 5,689,850 | A | | 11/1997 | Shekalim | |
| 5,842,249 | A | | 12/1998 | Sato | |
| 6,568,020 | B1 | | 5/2003 | Hosokawa | |
| 6,902,397 | B2 | | 6/2005 | Farrell et al. | |
| 7,716,771 | B2 | | 5/2010 | Kim | |
| 8,079,106 | B2 | | 12/2011 | Yang | |
| 8,239,991 | B2 | * | 8/2012 | Shimizu | A46B 15/0002 15/22.1 |
| 2004/0205914 | A1 | * | 10/2004 | Holden | A46B 13/02 15/22.1 |
| 2006/0265821 | A1 | * | 11/2006 | Hause | A46B 13/023 15/22.1 |
| 2012/0165710 | A1 | * | 6/2012 | Nichols | A61H 7/005 601/72 |
| 2013/0014331 | A1 | * | 1/2013 | Garner | A46B 9/045 15/22.1 |
| 2015/0173502 | A1 | * | 6/2015 | Sedic | A46B 9/04 15/22.1 |

* cited by examiner

*Primary Examiner* — Randall Chin
(74) *Attorney, Agent, or Firm* — Vincent Re PLLC

(57) ABSTRACT

A device is disclosed for providing a removable vibrating rubberized handle for a toiletry appliance. The device includes a vibrating motor insert and a rubberized handle. The rubberized handle includes at least one receiving cavity configured to receive at least one of a handle of the appliance and the vibrating motor insert.

9 Claims, 4 Drawing Sheets

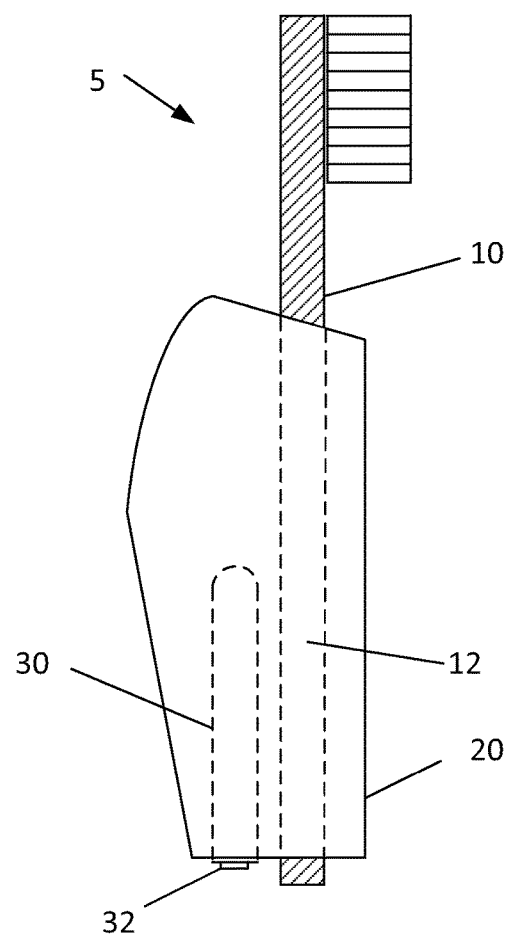
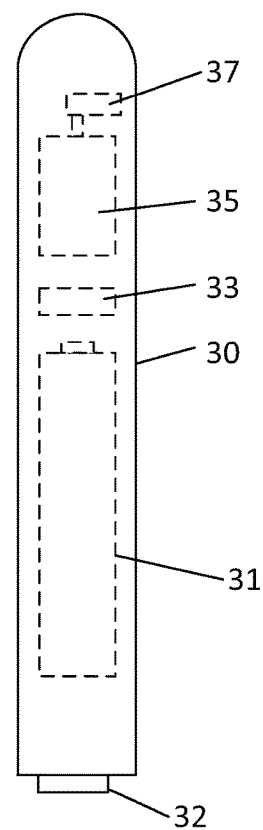
FIG. 2
FIG. 3

ELASTIC VIBRATING APPLIANCE HANDLE

CROSS REFERENCE TO RELATED APPLICATIONS

This disclosure claims the benefit of U.S. Provisional Application No. 62/049,413, filed on Sep. 12, 2014, which is hereby incorporated by reference.

FIELD OF THE DISCLOSURE

The present disclosure relates generally to an object for use in personal health and beauty care. In particular, examples of the present disclosure are related to an elastic handle including a vibrating motor accessory that can be fitted to a toiletry appliance or item such as a toothbrush, razor, hair brush, skin brush or shave cream brush.

BACKGROUND

The statements in this section merely provide background information related to the present disclosure. Accordingly, such statements are not intended to constitute an admission of prior art.

People use toiletry appliances to provide health and beauty care. People use toothbrushes to clean and care for teeth and oral health. People use razors to shave unwanted hair from their bodies. People use combs or brushes to style their hair and remove tangles. People use skin brushes to clean and remove skin cells and exfoliate the skin of the face and body. People use shave brushes to apply shaving products to the skin and hair prior to shaving.

Vibrating appliances such as vibrating toothbrushes are known. Such vibration can have a therapeutic, health, or customer satisfaction benefit. Such devices typically include large mechanisms built into the handle of the toothbrush. These devices can be large and awkward. If the vibrating mechanism mechanically fails, the whole toothbrush is thrown out. If the bristles on the toothbrush become worn out, then the whole toothbrush including the expensive vibrating mechanism must be thrown out. Further, the handle is typically made of the same hard plastic material of which the rest of the toothbrush is constructed.

SUMMARY

A device is disclosed for providing a removable vibrating rubberized handle for a toiletry appliance. The device includes a vibrating motor insert and a rubberized handle. The rubberized handle includes at least one receiving cavity configured to receive at least one of a handle of the appliance and the vibrating motor insert.

BRIEF DESCRIPTION OF THE DRAWINGS

One or more embodiments will now be described, by way of example, with reference to the accompanying drawings, in which:

FIG. 2 illustrates in the vibrating handle device of FIG. 1 installed to the disposable toothbrush, in accordance with the present disclosure;

FIG. 3 illustrates an exemplary vibrating motor insert, in accordance with the present disclosure;

Figure 1:
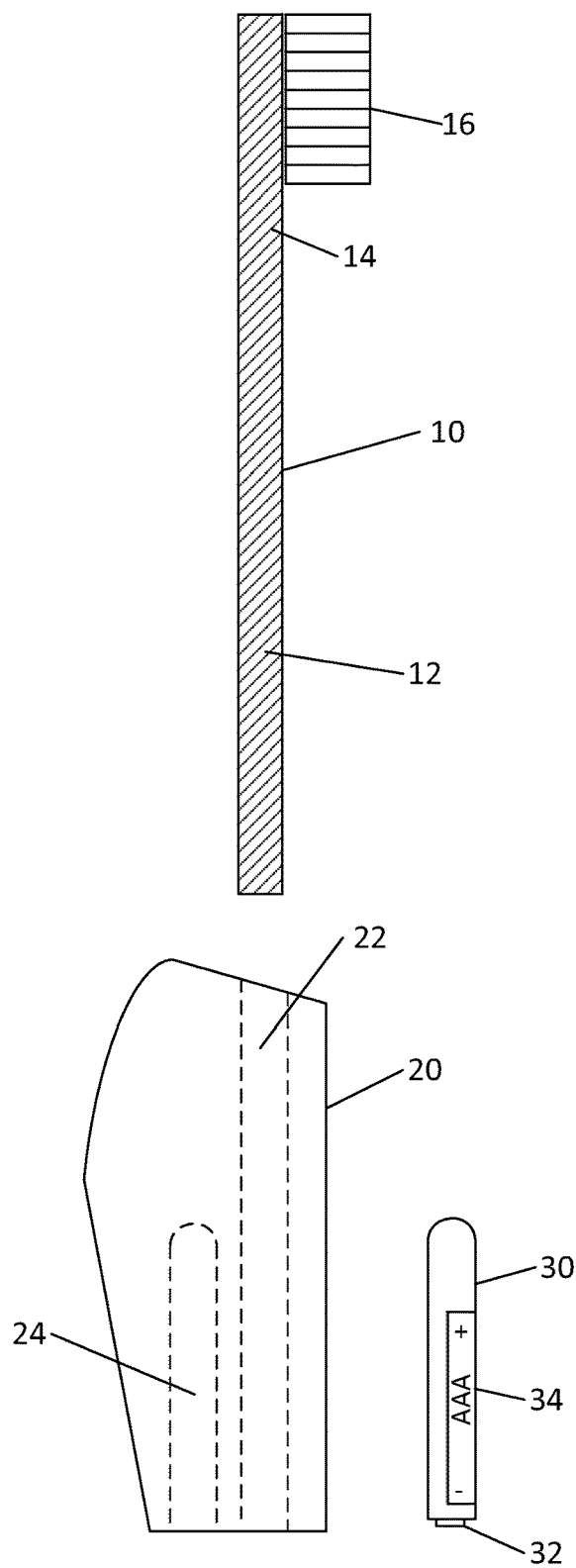
FIG. 1 illustrates an exemplary embodiment of a disposable toothbrush and a vibrating handle device, the handle shown separated from the toothbrush, in accordance with the present disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not illustrated in order to facilitate a less obstructed view of these various embodiments of the present disclosure.

DETAILED DESCRIPTION

In the following description, numerous specific details are set forth in order to provide a thorough understanding of the present disclosure. It will be apparent, however, to one having ordinary skill in the art that the specific detail need not be employed to practice the present disclosure. In other instances, well-known materials or methods have not been described in detail in order to avoid obscuring the present disclosure.

Reference throughout this specification to "one embodiment", "an embodiment", "one example" or "an example" means that a particular feature, structure or characteristic described in connection with the embodiment or example is included in at least one embodiment of the present disclosure. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale. Embodiments in accordance with the present disclosure may be embodied as an apparatus or process.

Toiletry appliances come in a wide variety of forms and functions. They can be disposable, intended to be discarded after a number of uses, or they can be reusable, for example, with a new fitting or set of blades that can be installed to an end of the appliance.

Vibration is used on some appliances like toothbrushes. Vibration can help agitate the bristles of the toothbrush to the teeth, causing relative motion between the two and aiding in the cleaning of the teeth. Vibration of toiletry appliances such as razors, hair brushes and skin brushes during use can stimulate the skin to beneficial effect.

Rubberized handles are known to improve a grip to an object in areas such as ergonomics and aesthetic appeal. In one example, a pliable rubber grip is known for use with a pencil, wherein the pencil is pushed into a hole in the grip and aligned such that the grip covers an area near to the tip of the pencil. The user holding the grip has the soft rubber between his or her fingers instead of the hard narrow shaft of the pencil. A better grip on a toiletry appliance can lead to higher user satisfaction.

An elastic vibrating appliance handle is disclosed which selectably vibrates a toiletry appliance item which is fitted to the elastic vibrating appliance handle. The elastic vibrating appliance handle includes a vibrating motor insert and a rubberized handle. The rubberized handle includes at least one receiving cavity configured to receive at least one of a handle of the toiletry appliance item and the vibrating motor insert.

According to one embodiment, the rubberized handle includes one receiving cavity configured to receive both the toiletry appliance item and the vibrating motor insert. According to another embodiment, the rubberized handle includes two receiving cavities, one configured to receive the toiletry appliance item and the other configured to receive the vibrating motor insert. According to a further embodiment, a control mechanism of the vibrating motor insert provides for pulsating vibration based on the user's selection. According to another embodiment, a control mechanism of the vibrating motor insert provides for variable intensity vibration based on the user's selection.

Grip housings or rubberized handles can be made of elastic material such as silicon, thermoplastic rubber (TPR), thermoplastic elastomer (TPE), or other similar materials. In one embodiment, the handle includes two cavities, one for an appliance being held and another for a vibrating motor insert. In another embodiment, the handle can include one cavity configured to receive both the appliance and the vibrating insert.

In some embodiments, cavity size can vary based on size of toiletry appliance and size of vibrating motor insert.

The vibrating insert or vibrating mechanism can include a battery and electric motor with an offset balance, such as are commonly used on pagers and cell phones, to create vibration on command. A control mechanism is provided, for example, including an on/off switch. The vibrating insert can include simple circuitry, for example, with a switch simply connecting a circuit between the battery and the motor. In another embodiment, circuitry enabling functionality such as pulsating vibration or variable intensity vibration can be provided, such as through use of a circuit board. In such embodiments, a user can select intervals of pulsating vibration depending on comfort or the ability to aid in effecting certain results.

FIG. 1 illustrates an exemplary embodiment of a disposable toothbrush and a vibrating handle device, the handle shown separated from the toothbrush. Disposable toothbrush 10 is illustrated including handle 12, shaft 14, and bristles 16. Vibrating insert 30 is illustrated including control mechanism 32 and battery cover 34. Handle 20 is illustrated including handle cavity 22 and vibrating insert cavity 24.

Handle 20 can be made of many different materials. According to one embodiment, handle 20 can be made of a transparent or translucent rubberized material. In another embodiment, the material is opaque. The material can be treated with a dye to color the handle. The handle can be provided or made available with different durometers or resistances to deformation, for example, with soft, medium, and hard handles covering a range of user preferences.

The handle can be provided or made available in different shapes, for example, with finger grips, to cover a range of user preferences. The handle can be provided or made available with different textures or patterns to aid the user's ability to grip the handle in a way that is appropriate for a particular action or task. The handle can be provided or made available in different sizes to accommodate toiletry appliances of various sizes, vibrating motor inserts of various sizes or user preference.

FIG. 2 illustrates the vibrating handle device of FIG. 1 installed to the disposable toothbrush. Assembled unit 5 is illustrated including the handle 12 of toothbrush 10 being inserted within handle 20. Additionally, vibrating insert 30 is inserted within handle 20. Control mechanism 32 of vibrating insert 30 is left exposed from handle 20 such that the user can activate, deactivate, or optionally modulate the operation of vibrating insert 30. Control mechanism 32 can include a binary on/off switch or button, a multi-position switch, a dial or knob, or any other control device known in the art.

FIG. 3 illustrates an exemplary vibrating motor insert. Vibrating insert 30 includes control mechanism 32, battery 31, optional circuit board 33, motor 35, and offset weight 37.

Figure 4:
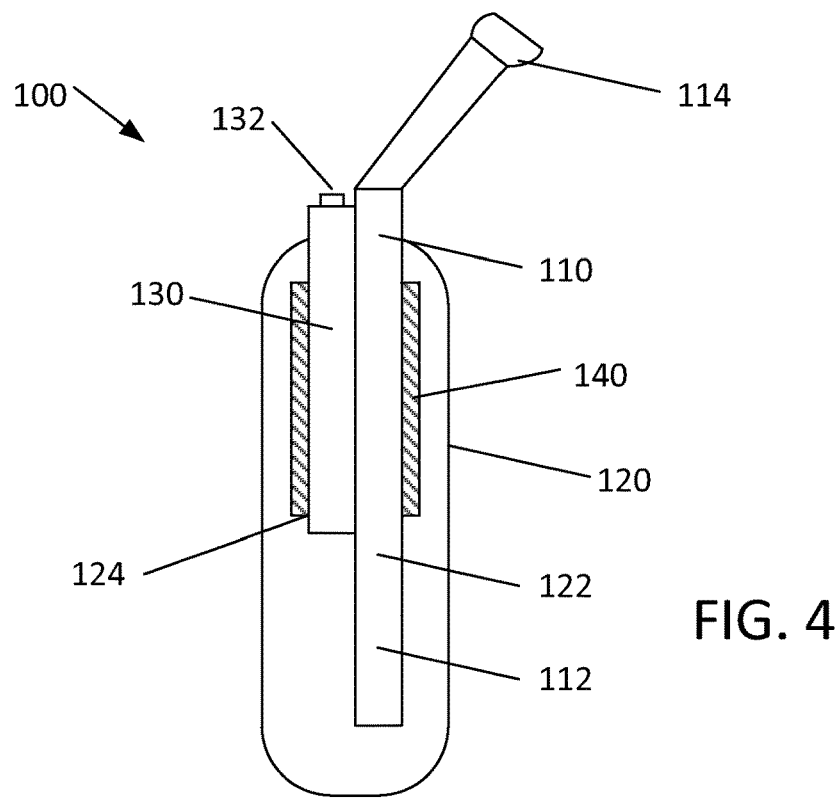
FIG. 4 illustrates an exemplary embodiment of a disposable razor and a vibrating handle device, in accordance with the present disclosure.

FIG. 4 illustrates an exemplary embodiment of a disposable razor and a vibrating handle device. Assembled unit 100 includes disposable razor 110, rubberized handle 120, and vibrating insert 130. Disposable razor 110 includes razor handle 112 and blade end 114. Handle 120 includes cavity 122 configured to hold razor handle 112 and cavity 124 configured to hold vibrating insert 130. Vibrating insert 130 includes control mechanism 132. Cavities 122 and 124 are formed together as a single cavity in handle 120 configured to receive both the razor handle 112 and the vibrating insert 130.

A rubberized handle with a cavity or cavities to receive a tool and a vibrating insert can be made of one material. Hollow plastic insert 140 is illustrated formed within rubberized handle 120, which includes a semi-cylindrical piece receiving both insert 130 and handle 112. Plastic insert 140 can be made of a harder or more rigid material than handle 120, such that insert 130 and handle 112 are held together tightly by insert 140, while the user still has the soft feel of the rubber material of handle 120.

One will appreciate that other devices, such as a double edge safety razor can be used with a similar handle to handle 120.

Figure 5:
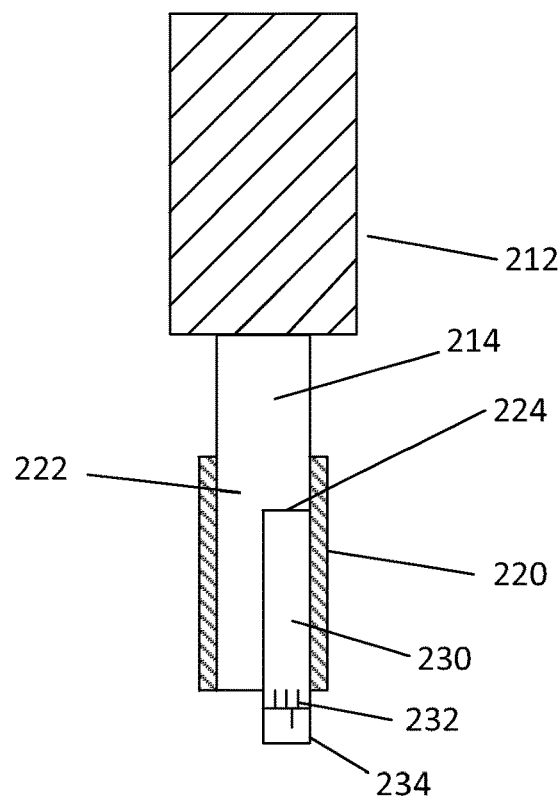
FIG. 5 illustrates an exemplary embodiment of a hairbrush and a vibrating handle device, in accordance with the present disclosure.

FIG. 5 illustrates an exemplary embodiment of a hairbrush and a vibrating handle device, in accordance with the present disclosure. Assembled unit 200 includes hairbrush 210, rubberized handle 220, and vibrating insert 230. Hairbrush 210 includes brush handle 214 and bristles 212. A cavity can be made within the rubberized handles disclosed herein for receiving the vibrating inserts disclosed herein. In the exemplary embodiment of FIG. 5, a specially configured hairbrush is provided with cavity 224 formed upon the handle 214, such that a thin rubberized handle 220 can be used around the handle while maintaining a similar cross-sectional width along the handle. Rubberized handle 220 includes cavity 222 configured to hold brush handle 214 and vibrating insert 230. Vibrating insert 230 includes control mechanism 232 embodied as a control knob 234.

Some embodiments of the invention disclosed herein may be used with skin brushes that are used to exfoliate the skin. Other embodiments may be used with shave brushes that are used to apply shaving products to the skin prior to shaving.

The vibrating motor insert can use normal, disposable, batteries. In one embodiment, the insert can include two exposed terminals, a connective terminal, or a plug in cord permitting the device to be charged or powered by an A/C outlet.

Figure 6:
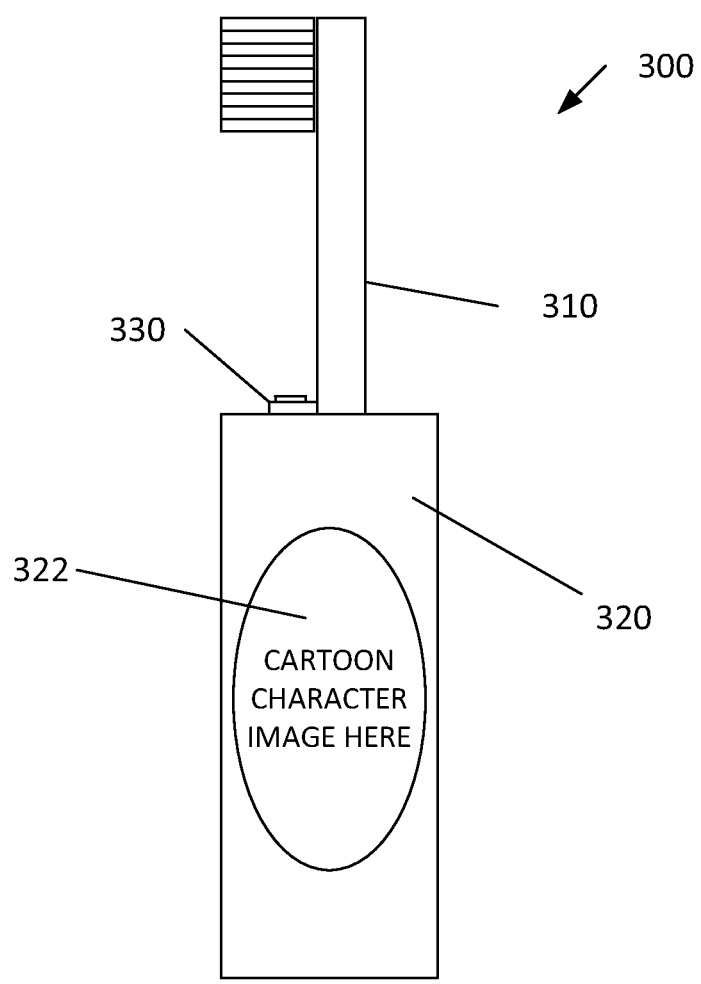
FIG. 6 illustrates an additional embodiment of a disposable toothbrush and a vibrating handle device, the handle shown including a decorative molded pattern upon an exterior surface.

FIG. 6 illustrates an additional embodiment of a disposable toothbrush and a vibrating handle device, the handle shown including a decorative molded pattern upon an exterior surface. Assembled unit 300 is illustrated including the handle of toothbrush 310 being inserted within handle 320. Additionally, vibrating insert 330 is inserted within handle 320. Control mechanism of vibrating insert 330 is left exposed from handle 320 such that the user can activate, deactivate, or optionally modulate the operation of vibrating insert 330. The body of handle 320 can include decorative patterns. For example, a mold in which the handle is formed can include texture or details configured to create many different patterns upon the handle. Portion 322 is illustrated whereupon a cartoon character or other decorative pattern could be created upon an exterior of the handle. In another embodiment, a particularly flat or smooth portion of the handle can be created to accept an adhesive sticker or other decorative addition to the handle.

The disclosure has described certain preferred embodiments and modifications of those embodiments. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

What is claimed is:

1. A device comprising a vibrating rubberized handle for a toiletry appliance, the device comprising:
    a vibrating motor insert; and
    a handle constructed entirely with elastic rubberized material, the handle comprising two receiving cavities, wherein at least one of the receiving cavities is configured to receive at least one of a handle of the appliance and the vibrating motor insert.

2. The device of claim 1, wherein the vibrating motor insert includes a battery and an electric motor with an offset balance.

3. The device of claim 2, wherein the vibrating motor insert includes a control mechanism.

4. The device of claim 3, wherein the control mechanism allows for variable intensity vibration.

5. The device of claim 3, wherein the control mechanism allows for pulsating vibration.

6. The device of claim 3, wherein the control mechanism allows for variable intensity vibration and pulsating vibration.

7. The device of claim 2, wherein the battery is inserted into the vibrating motor insert.

8. The device of claim 1, wherein the device is configured for use with a toothbrush.

9. A device comprising a vibrating rubberized handle for a toothbrush, the device comprising:
    a vibrating motor insert; and
    a handle constructed entirely with elastic rubberized material comprising:
        a first cavity configured to receive the toothbrush; and
        a second cavity configured to receive the vibrating motor insert.

* * * * *